(12) United States Patent
Zhang et al.

(10) Patent No.: US 9,337,626 B2
(45) Date of Patent: May 10, 2016

(54) CORONA DISCHARGE ASSEMBLY, ION MOBILITY SPECTROMETER, COMPUTER PROGRAM AND COMPUTER READABLE STORAGE MEDIUM

(71) Applicant: Nuctech Company Limited, Beijing (CN)

(72) Inventors: Qingjun Zhang, Beijing (CN); Yuanjing Li, Beijing (CN); Zhiqiang Chen, Beijing (CN); Yanchun Wang, Beijing (CN); Ziran Zhao, Beijing (CN); Yinong Liu, Beijing (CN); Yaohong Liu, Beijing (CN); Xiang Zou, Beijing (CN); Qiufeng Ma, Beijing (CN); Junxiao Wang, Beijing (CN); Xianghua Li, Beijing (CN); Jianping Chang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 14/577,211

(22) Filed: Dec. 19, 2014

(65) Prior Publication Data

US 2015/0188295 A1    Jul. 2, 2015

(30) Foreign Application Priority Data

Dec. 30, 2013    (CN) .......................... 2013 1 0741426

(51) Int. Cl.
*H01J 19/04*    (2006.01)
*H01T 19/00*    (2006.01)
(Continued)

(52) U.S. Cl.
CPC .............. *H01T 19/00* (2013.01); *G01N 27/622* (2013.01); *H01J 49/168* (2013.01)

(58) Field of Classification Search
None
See application file for complete search history.

(56) References Cited

U.S. PATENT DOCUMENTS 4,289,278 A * 9/1981 Itoh ........................... B05B 5/10
239/105
4,829,996 A * 5/1989 Noakes ................. A61M 15/02
128/200.14

(Continued)

FOREIGN PATENT DOCUMENTS

JP    DE 19903022 A1 * 10/1999 ................ A61L 9/22

*Primary Examiner* — Andrew Smyth
(74) *Attorney, Agent, or Firm* — McDermott Will & Emery LLP

(57) ABSTRACT

The present invention discloses a corona discharge assembly, an ion mobility spectrometer, an computer program and an computer readable storage medium. The corona discharge assembly includes: an ionization discharge chamber, wherein the ionization discharge chamber includes a metal corona cylinder, and the metal corona cylinder is provided with an inlet of a gas to be analyzed and a trumpet-shaped front port which is conductive to forming a gathered electric field; multiple corona pins, in which on-off of a high voltage can be independently controlled, are installed at the center of the metal corona cylinder in an insulating manner. The present invention further discloses an ion mobility spectrometer using the above-mentioned corona discharge assembly. The present invention can be used to prolong the service life of the integral corona discharge assembly; the discharge voltage of the ion source can be reduced and the discharge stability thereof can be improved; in comparison with the suspended installation of a pin-shaped electrode, since the multiple corona pins are fixed on the PCB, during installation, the position of the electrode can be accurate and stable, thus mass manufacture is easier to achieve.

13 Claims, 4 Drawing Sheets

(51) Int. Cl.
*G01N 27/62* (2006.01)
*H01J 49/16* (2006.01)

(56) References Cited

U.S. PATENT DOCUMENTS

| | | | | |
|---|---|---|---|---|
| 5,352,892 A * | 10/1994 | Mordehai | G01N 30/7266 | 250/288 |
| 5,485,016 A * | 1/1996 | Irie | H01J 49/0422 | 250/281 |
| 6,174,500 B1 * | 1/2001 | Uno | A61L 2/14 | 422/186.04 |
| 6,302,331 B1 * | 10/2001 | Dvorsky | A61M 15/02 | 239/3 |
| 6,454,193 B1 * | 9/2002 | Busick | A61L 9/14 | 239/3 |
| 6,508,982 B1 * | 1/2003 | Shoji | A61L 9/22 | 204/164 |
| 7,326,926 B2 * | 2/2008 | Wang | H01J 49/16 | 250/288 |
| 8,071,957 B1 * | 12/2011 | Ludwig | H01J 49/168 | 250/282 |
| 2004/0089802 A1 * | 5/2004 | Kato | H01J 49/145 | 250/285 |
| 2005/0109739 A1 * | 5/2005 | Destrez | H05H 1/24 | 219/121.54 |
| 2007/0007448 A1 * | 1/2007 | Wang | H01J 49/16 | 250/288 |
| 2007/0160389 A1 * | 7/2007 | Zona | G03G 15/0291 | 399/170 |
| 2008/0094772 A1 * | 4/2008 | Hino | H01T 4/16 | 361/130 |
| 2009/0189064 A1 * | 7/2009 | Miller | G01N 30/7206 | 250/282 |
| 2009/0236514 A1 * | 9/2009 | Renner | G01N 27/64 | 250/282 |
| 2010/0044581 A1 * | 2/2010 | Fujita | H01T 23/00 | 250/424 |
| 2010/0075317 A1 * | 3/2010 | Schneider | B03C 3/383 | 435/6.12 |
| 2010/0096542 A1 * | 4/2010 | Whitehouse | H01J 49/0431 | 250/282 |
| 2010/0314548 A1 * | 12/2010 | Munchmeyer | G01N 27/624 | 250/375 |

* cited by examiner

CORONA DISCHARGE ASSEMBLY, ION MOBILITY SPECTROMETER, COMPUTER PROGRAM AND COMPUTER READABLE STORAGE MEDIUM

TECHNICAL FIELD

The present invention relates to the filed of security detection technology, in particular, to a multi-pin corona discharge assembly, which is convenient to manufacture and is long in service life, an ion mobility spectrometer used for detecting narcotics and explosives and utilizing the assembly as an ionization source, corresponding computer program and computer readable storage medium.

BACKGROUND

An ion mobility spectrometer resolves ions according to different drift velocities of different ions under a uniform weak electric field. It has the advantages of high resolution speed, high sensitivity, free of a vacuum environment and convenience for miniaturization, thus being widely applied to the detection field of narcotics and explosives. A typical ion mobility spectrometer is generally composed of a sample introduction part, an ionization part, an ion gate, a migration area, a collection area, a readout circuit, a data collecting and processing part, a control part and the like, wherein the main function of the ionization part is to transform sample molecules into ions for migration and separation, thus the ionization effect has very direct influence on the performance of the spectrometer. In the prior art, the most common and most widely used ionization assembly is a $^{63}$Ni radioactive source, which has the advantages of small volume, high stability and no additional circuit, but also has the problems of narrow linear range, low ion transformation concentration and radiation pollution. Especially, the radiation pollution problem brings a lot of inconvenience to operation, transportation and management of equipment. In order to overcome the above-mentioned problems, corona discharge technology is adopted to replace radioactive source technology. Corona discharge refers to a phenomenon of gas molecule separation induced by a local strong electric field in a non-uniform electric field in the space. Ions directly generated by corona discharge are generally called reactant ions, when sample molecules with higher protons or electron affinity pass by the ionization area, the sample molecules capture the charges of the reactant ions to be ionized. In general, a corona discharge structure is relatively simple, so the cost is low; meanwhile, the concentration of charges generated by corona discharge is much higher than that of the radioactive source, thereby being beneficial to improving the sensitivity of the ion mobility spectrometer and obtaining a larger dynamic range. Application examples of corona discharge serving as the ionization source of the ion mobility spectrometer are reported in U.S. Pat. No. 5,485,016 and CA2124344 and Chinese patents CN1950698A and CN103137417A. A common corona discharge structure 100 has a discharge form of pinpoint-flat plate or pinpoint-cylinder, as shown in FIGS. 1A and 1B. The fixed tail end of a corona pin realizing discharge is usually installed on a supporting matrix, and the tail end is connected to a high voltage power supply; the other end of the corona pin is a free end (i.e., a pinpoint) and is generally a tip 102 with a very small radius of curvature (smaller than 0.1 mm). A non-uniform electrostatic field is formed in the space between a flat or cylindrical electrode and the pinpoint, such that the electric field intensity near the pinpoint is very high, and the electric field intensity of the space away from the pinpoint progressively decreases. Gas ionization only occurs in the space close to the surface of the free tip of the electrode, the ionization area is very small, thus the generated ion concentration is quite small as well; if the ionization area is increased, a higher voltage is needed, and the requirement on the high voltage power supply is very high. In addition, under the condition that only one tip discharges, the corona discharge will generate oxidation on a corona electrode, after long term operation, chemical reactions resulting from water vapor or the like in the gas will severely corrode the tip to increase the radius of curvature thereof, thus increasing the voltage threshold of the corona discharge, reducing the corona discharge stability and leading to the end of service life; furthermore, in order to achieve a smaller radius of curvature, the diameter of the pin is very small in general, the strength is quite low, thus it is very difficult to keep a higher position precision during manufacture and assembly of a product. In order to improve this situation, a multi-pin corona discharge structure is developed.

U.S. Pat. No. 7,326,926B2 describes a typical multi-pin cluster corona discharge ion source, as shown in FIG. 1C. A cluster 106 of parallel corona pins is adopted to replace a single corona pin of the typical corona discharge ion source 104; due to the design of simultaneously loading a high voltage on multiple tips of the multi-pin cluster to discharge, the problem of reduced service life of the ionization source caused by discharge failure of the single corona pin is eased to a certain degree. However, the design of simultaneously loading the high voltage on the multiple tips to discharge also has obvious disadvantages. Firstly, the high voltage is simultaneously loaded on multiple pins, electric fields formed by the pins will influence each other to reduce the electric field intensity at the pinpoints, thus a corona voltage needs to be improved, as a result, a higher requirement is proposed on the high voltage power supply; in addition, due to the processing inconsistency, the shapes and surface conditions of the tips are different, all tips cannot be guaranteed to meet a corona discharge condition, the pin with a relatively small radius of curvature firstly discharges and is gradually corroded to result in gradual increasing the radius of curvature thereof to fail to meet the corona discharge condition, and the rest pins meeting the condition begin to discharge, in this case, how many pins generate corona discharge at a moment cannot be guaranteed, with high stochastic property, so that the change of the number of ions generated by ionization is very large, resulting in unstable corona discharge, which is not conducive to the stable work of the ion mobility spectrometer.

SUMMARY

The inventor realizes that, if multiple pins can be singly controlled to alternately perform corona discharge, namely, at a moment, only one pin is loaded with a high voltage to generate the corona discharge and the rest pins are loaded with no high voltage, a strong electric field is easy to form at the pinpoint loaded with the high voltage, and the problems of instability of a corona ion source caused by simultaneously loading the high voltage on multiple pins and a short service life of a single-pin corona ion source can be solved at the same time.

The object of the present invention is to provide a design solution of an alternate corona discharge assembly, which is stable and is convenient to manufacture and in which multiple pins are independently controlled, and the design is simple in structure and can be used for effectively prolonging the overall service life of an ionization assembly, improving the stability of corona discharge and improving the performance of a mobility spectrometer.

In order to achieve the above-mentioned purpose, according to the embodiment of the present invention, the corona discharge assembly includes an ionization discharge chamber, wherein the ionization discharge chamber includes a metal corona cylinder, and the metal corona cylinder is provided with an inlet of a gas to be analyzed and a trumpet-shaped front port which is conductive to forming a gathered electric field; multiple corona pins, in which on-off of a high voltage can be independently controlled, are installed at the center of the metal corona cylinder in an insulating manner. Therefore, multiple pins can be singly controlled to alternately perform corona discharge, namely, at a moment, only one pin is loaded with the high voltage to generate the corona discharge and the rest pins are loaded with no high voltage, the strong electric field is easy to form at the pinpoint loaded with the high voltage, and the problems of instability of the corona ion source caused by simultaneously loading the high voltage on multiple pins and the short service life of the single-pin corona ion source can be solved at the same time.

Preferably, the corona discharge assembly includes a PCB, and the PCB is used for fixing the corona pin.

Preferably, the PCB is a high temperature resistant PCB with a wiring layer clamped between two insulating layers; multiple uniformly distributed via holes are formed in the front end of the PCB, wherein the assembly position of the via hole at the center thereof is located on the axial line of the metal corona cylinder, and a corona pin is brazed in each via hole.

Preferably, each via hole is connected with a single conducting wire.

Preferably, the single conducting wire is a PCB copper clad conducting wire, and independent high voltage conducting wires are respectively welded at the tail end thereof, in order to be connected with an external high voltage power supply.

Preferably, the on-off of each high voltage conducting wire can be singly controlled. When the corona ion source is at work, the corona pins on the PCB are controlled by an external switch to be alternately loaded with the high voltage so as to generate corona discharge at the tips thereof. When all corona pins on one PCB are ineffective, the assembly can be detached for replacement of a new PCB or replacement and brazing of new corona pins.

Preferably, the corona discharge assembly further includes an ion reaction and storage ring, wherein the ion reaction and storage ring is an internal passage with a shape like a trumpet, the small opening end of the ion reaction and storage ring is embedded in the trumpet-shaped opening of the metal corona cylinder, but is not in electrical contact with the metal corona cylinder, and the large opening end of the ion reaction and storage ring is in contact with a first grid of an ion gate to form an equipotential area between the interior of the large opening end and the first grid of the ion gate, in order to store ions. Therefore, the ions generated by corona discharge can enter an ion reaction and storage area under the traction of the electric field. The main functions of the ion reaction and storage ring are as follows: when the ion gate is closed, ensuring full reaction and compound between primary action ions and a sample gas and generating and storing a characteristic ion cluster to be detected; and when the ion gate is open, focusing the compounded ion cluster and driving the ion cluster to enter an ion migration cavity through the ion gate. By means of the design, corona discharge impulse interference can be effectively shielded, the fluctuation of the number of ions caused by corona impulse is shielded, the pass rate of the ions at the ion gate is increased, and an effect of stabilizing an ion mobility spectrum line is achieved.

According to the embodiment of the present invention, an ion mobility spectrometer is further disclosed, the ion mobility spectrometer includes: the above-mentioned corona discharge assembly; an ion gate composed of two opposite grids; a migration area, wherein the migration area includes drift electrodes, and the drift electrodes are concentric equidistant circular ring electrodes; and a Faraday disc, wherein the rear of the Faraday disc is connected with a charge sensitive amplifier to read ion signals.

According to the embodiment of the present invention, a computer program for corona discharge assembly is further disclosed. In order to control corona discharging of the corona discharge assembly, the computer program comprises the following step:

wherein, only one corona pin generates corona discharge at any moment, the rest pins are suspended, and the multiple pins are alternately loaded with the high voltage to work.

According to the embodiment of the present invention, a computer readable storage medium for storing the computer program is further disclosed.

Due to the corona discharge assembly, the ion mobility spectrometer, the computer program and the computer readable storage medium according to the present invention, at any moment, only one corona pin generates corona discharge, the rest pins are suspended, and the multiple pins are alternately loaded with the high voltage to work, thus compared with a single-pin structure, the structure can be used for prolonging the service life of the integral corona discharge assembly; compared with a multi-pin cluster structure, the discharge voltage of the ion source can be reduced and the discharge stability thereof can be improved; in comparison with the suspended installation of a pin-shaped electrode, since the multiple corona pins are fixed on the PCB, during installation, the position of the electrode can be accurate and stable, thus mass manufacture is easier to achieve.

DETAILED DESCRIPTION OF THE PREFERRED EMBODIMENTS

To make the objective, structures and advantages of the present invention clearer, the present invention will be further described as below in details with reference to the accompanying drawings. The embodiments below are described for illustration only, not for limiting the scope of the invention.

Figure 1A:
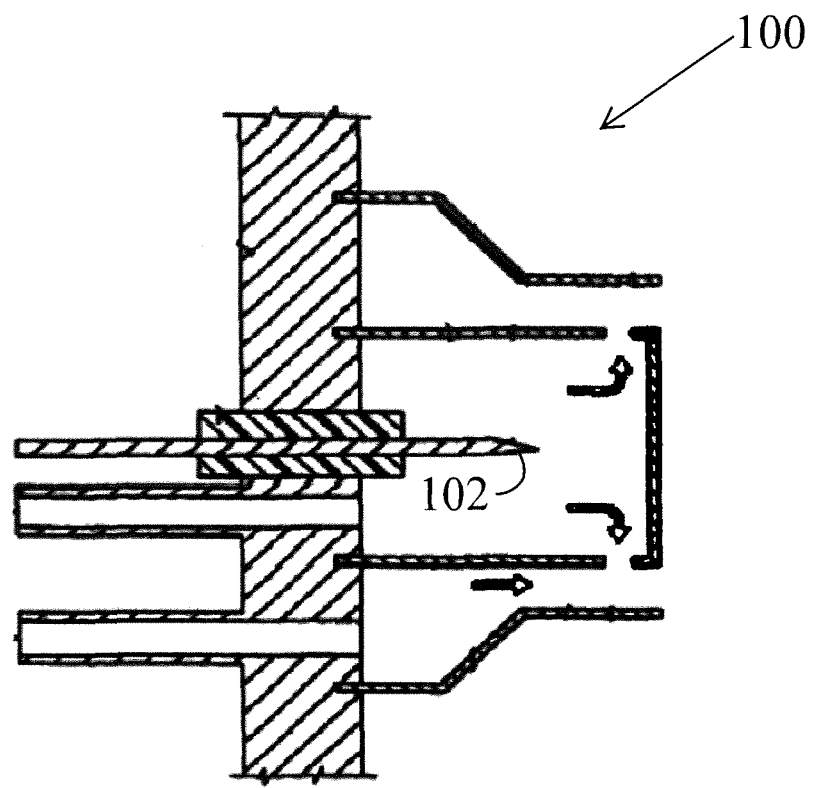
FIGS. 1A, 1B and 1C are schematic diagrams of a structure of a traditional corona discharge structure.
Figure 1B:
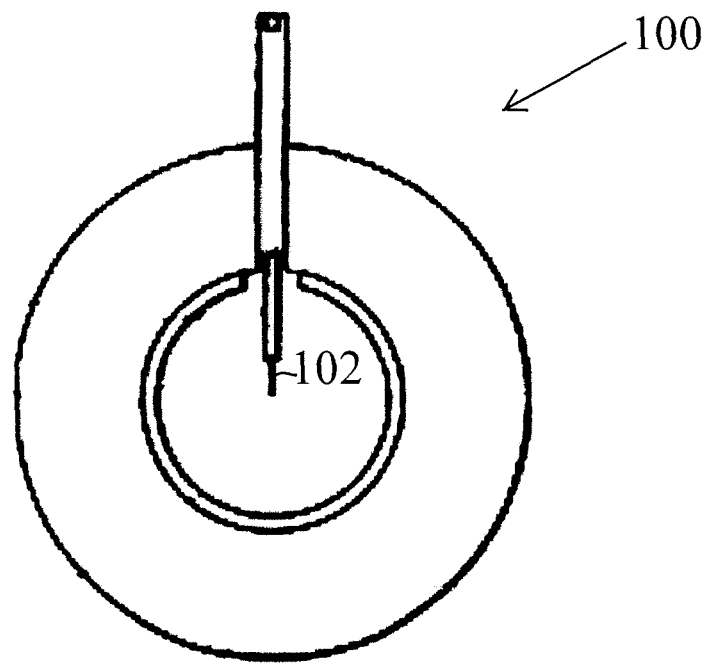
Figure 1C:
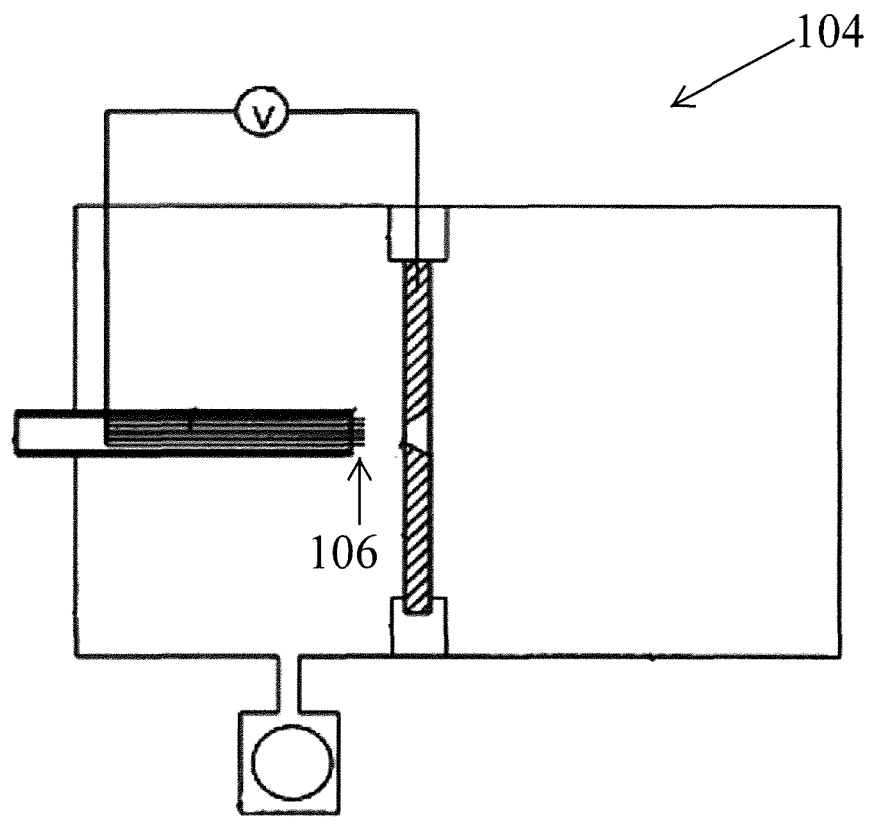
Figure 2A:
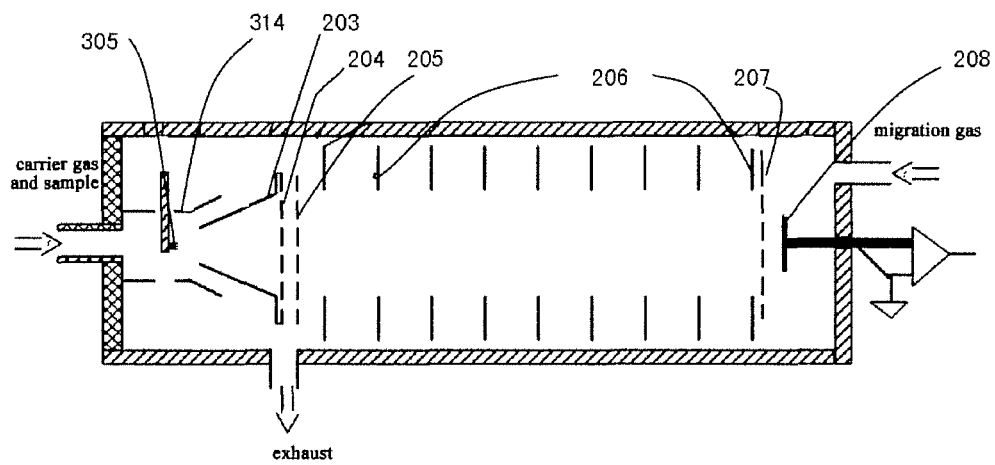
FIG. 2A is a schematic diagram of a structure of an ion mobility spectrometer using a PCB multi-pin alternate corona discharge ion source assembly according to an embodiment of the present invention.

In the corona discharge ion mobility spectrometer as shown in FIG. 2A, a non-uniform electric field achieving corona discharge is mainly formed by corona pins 305, a metal corona cylinder 314 and an ion reaction and storage ring 203. The ion mobility spectrometer includes: a corona discharge assembly; an ion gate composed of two opposite grids 204, 205; a migration area, wherein the migration area includes drift electrodes 206, and the drift electrodes 206 are concentric equidistant circular ring electrodes; and a Faraday disc 208, wherein the rear of the Faraday disc 208 is connected with a charge sensitive amplifier to read ion signals.

According to the embodiment of the present invention, the corona discharge assembly includes an ionization discharge chamber, wherein the ionization discharge chamber includes the metal corona cylinder 314, and the metal corona cylinder 314 is provided with an inlet (shown on the left side of FIG. 2A) of a gas to be analyzed and a trumpet-shaped front port which is conductive to forming a gathered electric field; multiple corona pins 305, in which on-off of a high voltage can be independently controlled, are installed at the center of the metal corona cylinder 314 in an insulating manner.

Wherein, the on-off of the high voltage of the corona pins 305 is independently controlled, and each of the multiple corona pins 305 is singly connected to a high voltage conducting wire, in which on-off can be singly controlled. Therefore, multiple pins 305 can be singly controlled to alternately perform corona discharge, namely, at a moment, only one corona pin 305 is loaded with the high voltage to generate the corona discharge and the rest corona pins 305 are loaded with no high voltage, the strong electric field is easy to form at the pinpoint of the corona pins 305 loaded with the high voltage, and the problems of instability of the corona ion source caused by simultaneously loading the high voltage on multiple pins and the short service life of the single-pin corona ion source can be solved at the same time.

Figure 2B:
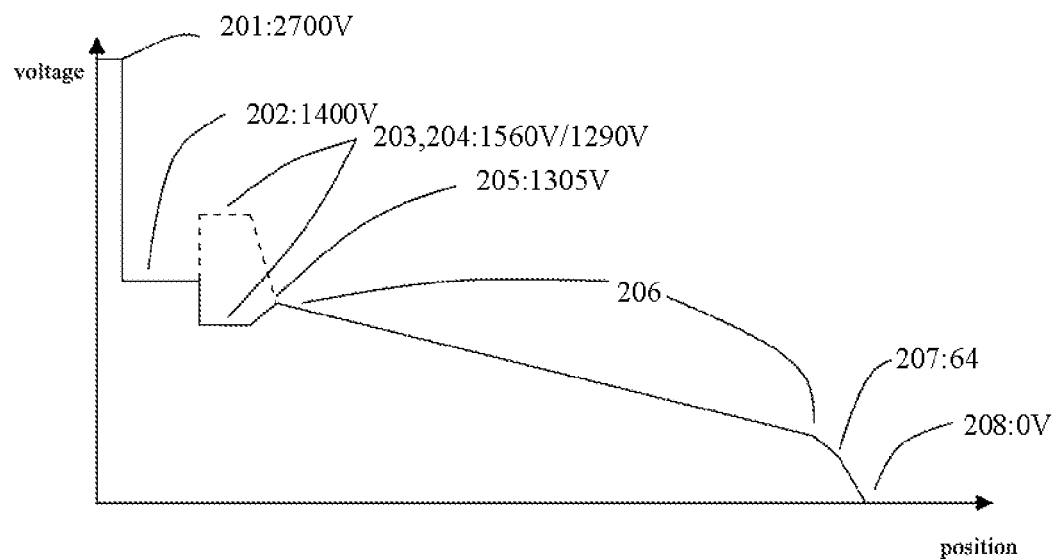
FIG. 2B is a schematic diagram of potentials of electrodes of the ion mobility spectrometer in FIG. 2A under a forward mode.

FIG. 2B is a schematic diagram of potentials of electrodes of the ion mobility spectrometer in FIG. 2A under a forward mode. When the ion mobility spectrometer is at work, the voltage of each corona pin 305 is about 700-3000 V (determined by the radius of the tip of the corona pin 305 and the length of the corona pin 305, different geometry sizes corresponding to different discharge inception voltages) higher than the voltage of the metal corona cylinder 314 to produce corona, so as to generate ions. The voltage of the ion reaction and storage ring 203 and a first ion gate 204 periodically hops, see FIG. 2B, it can be called a storage state (i.e., a full line part) when at a low voltage, and is called a traction state (i.e., a dotted line part) when at a corresponding high voltage. When the voltage of the ion reaction and storage ring 203 and the first ion gate 204 is at the storage state, the voltage is 60-150V lower than the voltage of the metal corona cylinder 314 and is about 5-60V lower than the voltage of a second ion gate 205, after entering the first ion gate 204, the ions are subject to weaker electric field force, and mainly perform thermal motion in the cavity of the first ion gate 204; after the ions in the first ion gate 204 are accumulated to a certain number over certain time, the voltage of the ion reaction and storage ring 203 and the first ion gate 204 hops to the traction state, at this time, the ions generated by corona at the corona pin 305 stop entering the first ion gate 204 (in order to prevent the fluctuation of the number of the ions in the first ion gate 204 caused by corona impulse), and the ions in the first ion gate 204 quickly enter the ion migration area 206 through the second ion gate 205 under the action of the electric field between the first ion gate 204 and the second ion gate 205. In the ion migration area 206 filled with a migration gas through a migration gas inlet (as shown on the right side in FIG. 2A), the ions achieve a symmetrical motion state under the coaction of electric field traction and reversely moving migration gas flow, after a long migration distance, the ions with different migration rates are separated due to different velocities and are finally collected by a Faraday disc 208 after passing by an inhibition grid 207 and are recorded by a rear end circuit. The gas in the ion mobility spectrometer is discharged from a gas outlet shown in the lower side of FIG. 2A.

Figure 3A:
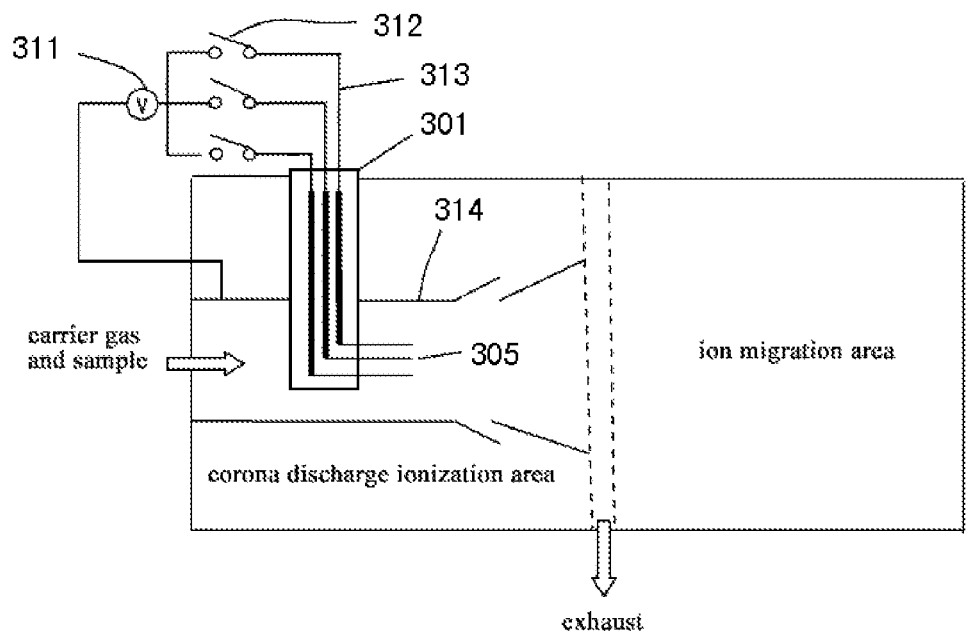
FIG. 3A is a schematic diagram of high voltage connection of a multi-pin alternate discharge ion source according to an embodiment of the present invention.
Figure 3B:
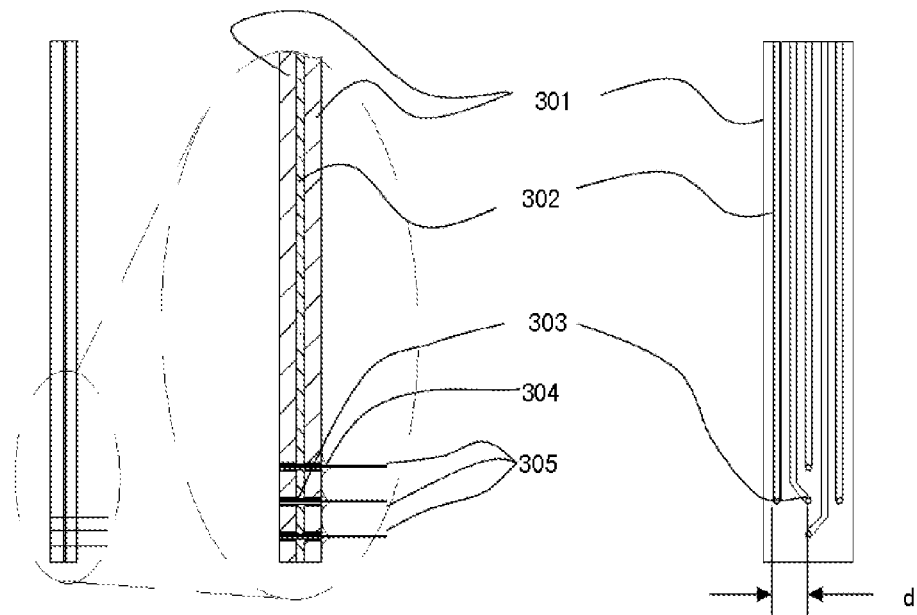
FIG. 3B is a cross-sectional diagram of a side face and a facade of a PCB of a corona discharge assembly according to an embodiment of the present invention.

FIG. 3A is a schematic diagram of high voltage connection of a multi-pin alternate discharge ion source according to an embodiment of the present invention; FIG. 3B is a cross-sectional diagram of a side face and a facade of a PCB of a corona discharge assembly according to an embodiment of the present invention. Preferably, the corona discharge assembly includes a PCB 301 used for fixing the corona pins 305 with the function of a high voltage connecting seat.

Preferably, the PCB 301 is a high temperature resistant PCB with a wiring layer clamped between two insulating layers; multiple uniformly distributed via holes 303 are formed in the front end (namely, in a position near the axial line of the metal corona cylinder) of the PCB 301, wherein the assembly position of the via hole at the center thereof is located on the axial line of the metal corona cylinder 314, and a corona pin 305 is brazed in each via hole 303.

Preferably, each via hole 303 is connected with a single conducting wire 302. The single conducting wire 302 is a PCB copper clad conducting wire, and independent high voltage conducting wires 313 are respectively welded at the tail end thereof in order to be connected with an external high voltage power supply. The on-off of each high voltage conducting wire 313 can be singly controlled. When the corona ion source is at work, the corona pins 305 on the PCB are controlled by an external switch to be alternately loaded with the high voltage so as to generate corona discharge at the tips thereof. When all corona pins 305 on one PCB are ineffective, the assembly can be detached for replacement of a new PCB electrode board or replacement and brazing of new corona pins 305.

The corona discharge assembly can further include an ion reaction and storage ring 203, wherein the ion reaction and storage ring 203 is an internal passage with a shape like a trumpet, the small opening end of the ion reaction and storage ring 203 is embedded in the trumpet-shaped opening of the metal corona cylinder 314, but is not in electrical contact with the metal corona cylinder 314, and the large opening end of the ion reaction and storage ring 203 is in contact with a first grid 204 of an ion gate to form an equipotential area between the interior of the large opening end and the first grid 204 of the ion gate, in order to store ions. Therefore, the ions generated by corona discharge can enter an ion reaction and storage area under the traction of the electric field. The main functions of the ion reaction and storage ring are as follows: when the ion gate is closed, ensuring full reaction and compound between primary action ions and a sample gas and generating and storing a characteristic ion cluster; and when the ion gate is open, focusing the compounded ion cluster and driving the ion cluster to enter an ion migration cavity through the ion gate. By means of the design, corona discharge impulse interference can be effectively shielded, the fluctuation of the number of ions caused by corona impulse is shielded, the pass rate of the ions at the ion gate is increased, and an effect of stabilizing an ion mobility spectrum line is achieved.

The PCB can be a PCB prepared by clamping the wiring layer between two high temperature resistant insulating layers, the PCB 301 has good insulating property and high temperature resistance, can be resistant to a high voltage of 4000 V and resistant to a high temperature of at least 180° C., is stable in chemical property and contains no volatile substance. The material of the PCB 301 can be ceramic, polyimide or the like. The PCB electrode board is provided with multiple via holes 303 (preferably 4-7) uniformly distributed at a certain distance d in the end (namely, in positions near the axial line of the metal corona cylinder 314) inserted into the corona cylinder, each via hole 303 is connected with one printing conducting wire 302, and the printing conducting wires 302 are not interconnected, the other end of the PCB 301 is stretched out from the metal corona cylinder 314, each printing conducting wire 302 on the PCB 301 is connected with a high voltage power supply 313 through a single high voltage conducting wire 313, and each high voltage conducting wire 313 is provided with an independent switch 312. A corona pin 305 is fixed in each via hole 303 in a brazing manner through a high temperature solder 304. The corona pins 305 can be needle-like or filiform, each have a very thin tip (the radius of curvature is smaller than 0.05 mm), and can be made from chemically inert refractory metal, such as platinum or iridium or the like; the heights of the corona pins 305 exceeding the PCB are uniform. The distance d between the corona pins 305 is arranged by comprehensively considering the minimal PCB hole distance capable of being achieved by the processing technique and the influence of the wire electrode eccentric distance on the pass rate of the ions at the ion gate. During corona discharge, a voltage is loaded on one of the corona pins 305, the rest pins are suspended, a non-uniform corona electric field is formed among the corona pin 305 loaded with the voltage, the metal corona cylinder 314 and the ion reaction and storage ring 203, the electric field intensity at the tip of the corona pin 305 with a small radius of curvature is high, and corona discharge is generated on the surface space thereof. When the pinpoint of the corona pin 305 to be discharged becomes ineffective due to bombardment of charged particles or corrosion, replacement can be performed so that another corona pin 305 is loaded with a high voltage, and the rest pins 305 are suspended. In this way, the corona pins 305 alternately generate corona discharge, so as to prolong the integral service life of the corona discharge assembly. The corona pins 305 can be installed on the PCB in a brazing manner, the processing precision of the PCB is high, and the strength is high, and the corona pins 305 are fixed in the brazing manner, thus being very convenient to install, change and maintain.

EXAMPLES

Figure 4:
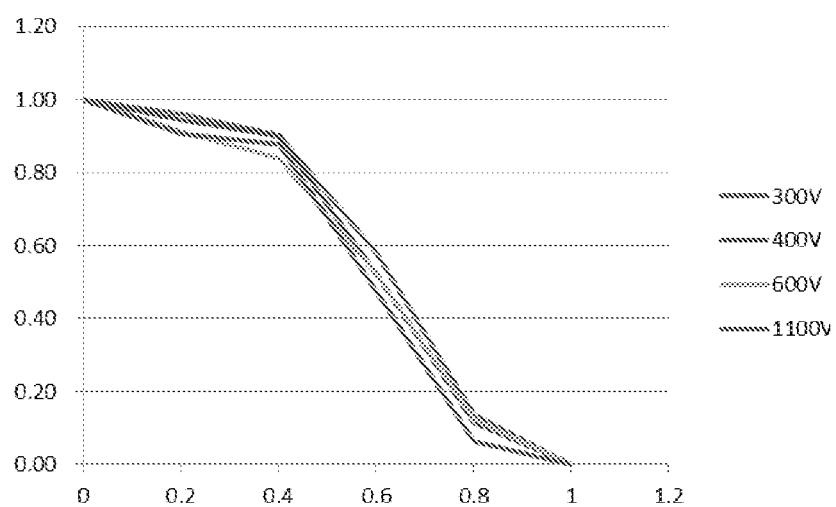
FIG. 4 is a diagram showing change of a relative ion pass rate with a wire electrode eccentric distance in the case of different ion gate leaping voltages.

In the example, a specific design of replacing the corona discharge assembly of an axial suspended slender corona pin 305 in a traditional corona discharge structure with a PCB brazing corona pin is described. The PCB as shown in FIG. 3B is made from two aluminum oxide ceramic insulating layers 301 and a wiring layer 302, the thickness of each insulating layer is 1 mm, and the thickness of the intermediate wiring layer is 2 OZ (about 0.07 mm) Five via holes 303 with diameters of 0.2 mm are formed in one end of the PCB, when being installed, one via hole 303 is located at the axial center of the metal corona cylinder 314, the rest four holes are symmetrical with the center hole as the center and are uniformly distributed surrounding the same, and the distance d between each via hole 303 and the center hole is 0.4 mm. One corona pin 305 is vertically brazed in each via hole through the high temperature solder; the corona pin 305 is made from a platinum wire with a diameter of 20-50 μm, and the height of the corona pin 305 exceeding the PCB is 2 mm. For the example, the printing wire width/distance of the PCB is 8/8 mil (about 0.2 mm), and the distance between the via holes 303 (namely, the eccentric distance of all corona pins 305) is 0.4 mm. According to an analog calculation result, when the eccentric distance of the corona pin 305 loaded with the high voltage is within 0.4 mm, compared with the corona pin 305 loaded with the high voltage and located at the center, the relative ion pass rate can be up to 0.9, as shown in FIG. 4.

Due to the structural features of the corona discharge assembly according to the present invention, at any moment, only one corona pin 305 generates corona discharge, the rest pins 305 are suspended, and the multiple pins 305 are alternately loaded with the high voltage to work, thus compared with a single-pin structure, the structure can be used for prolonging the service life of the integral corona discharge assembly; in comparison with a multi-pin cluster structure, the discharge voltage of the ion source can be reduced and the discharge stability thereof can be improved; compared with the suspended installation of a pin-shaped electrode, since the multiple corona pins are fixed on the PCB, during installation, the position of the electrode can be accurate and stable, thus mass manufacture is easier to achieve.

According to the embodiment of the present invention, a computer program for corona discharge assembly is further disclosed. In order to control corona discharging of the corona discharge assembly, the computer program comprises the following step: wherein, only one corona pin generates corona discharge at any moment, the rest pins are suspended, and the multiple pins are alternately loaded with the high voltage to work.

According to the embodiment of the present invention, a computer readable storage medium for storing the computer program is further disclosed.

Based on above contents, corona discharge assembly, the ion mobility spectrometer, the computer program and the computer readable storage medium according to the present invention, at any moment, only one corona pin generates corona discharge, the rest pins are suspended, and the multiple pins are alternately loaded with the high voltage to work, thus compared with a single-pin structure, the structure can be used for prolonging the service life of the integral corona discharge assembly; compared with a multi-pin cluster structure, the discharge voltage of the ion source can be reduced and the discharge stability thereof can be improved; in comparison with the suspended installation of a pin-shaped electrode, since the multiple corona pins are fixed on the PCB, during installation, the position of the electrode can be accurate and stable, thus mass manufacture is easier to achieve.

The present invention can be implemented in any suitable form, including hardware, software, firmware or any combination thereof. Optionally, the present invention can be at least partially implemented as computer software running on one or multiple data processors and/or digital signal processors. The elements and components in the embodiment of the present invention can be physically, functionally and logically implemented in any suitable form. In fact, the functions can be implemented in a single unit, in multiple units or as a part of other functional units. Similarly, the present invention can be implemented in a single unit or can be physically and functionally distributed between different units and processors.

Although the present invention has been described in combination with some embodiments, the present invention is not intended to be limited to the specific form set forth herein. On the contrary, the scope of the present invention is only limited by the appended claims. Additionally, although the features may appear to be described in combination with particular embodiments, those skilled in the art should recognize that the various different features of the described embodiments can be combined according to the present invention. In the claims, the wording including/containing does not exclude the presence of other elements or steps.

Furthermore, although individually listed, a plurality of devices, elements or method steps can be implemented by, for example, a single unit or a processor. Additionally, although the individual features can be included in different claims, these features can be combined advantageously, and its inclusion in different claims does not imply that the combination of the features is not feasible and/or advantageous. In addition, the inclusion of the features in a claim category does not imply it is limited to this category, but indicates that the features can be suitably applied to other claim categories as well. Furthermore, the sequence of the features in the claims does not imply any specific sequence in which the features must work.

INDUSTRIAL APPLICABILITY

The corona discharge assembly, the ion mobility spectrometer, the computer program and the computer readable storage medium according to the present invention can be used for prolonging the service life of the integral corona discharge assembly; compared with a multi-pin cluster structure, the discharge voltage of the ion source can be reduced and the discharge stability thereof can be improved; in comparison with the suspended installation of a pin-shaped electrode, since the multiple corona pins are fixed on the PCB, during installation, the position of the electrode can be accurate and stable, thus mass manufacture is easier to achieve.

What is claimed is:

1. A corona discharge assembly, characterized in that, the corona discharge assembly comprises:
    an ionization discharge chamber, wherein the ionization discharge chamber comprises a metal corona cylinder, and the metal corona cylinder is provided with an inlet of a gas to be analyzed and a trumpet-shaped front port which is conductive to forming a gathered electric field;
    multiple corona pins, in which on-off of a high voltage can be independently controlled, are installed at the center of the metal corona cylinder in an insulating manner, wherein the trumpet-shaped front port expands in diameter in a direction away from the corona pins; and
    an ion reaction and storage ring, wherein the ion reaction and storage ring is an internal passage that is trumpet-shaped, and the small opening end of the ion reaction and storage ring is embedded in the larger end of the trumpet-shaped opening of the metal corona cylinder.

2. The corona discharge assembly according to claim 1, characterized in that, the corona discharge assembly further comprises a PCB for fixing the corona pin.

3. The corona discharge assembly according to claim 2, characterized in that, the PCB is a high temperature resistant PCB with a wiring layer clamped between two insulating layers.

4. The corona discharge assembly according to claim 2, characterized in that, multiple uniformly distributed via holes are formed in the front end of the PCB, wherein the assembly position of the via hole at the center thereof is located on the axial line of the metal corona cylinder, and a corona pin is brazed in each via hole.

5. The corona discharge assembly according to claim 4, characterized in that, the eccentric distance of all corona pins is 0.4 mm.

6. The corona discharge assembly according to claim 4, characterized in that, each via hole is connected with a single conducting wire.

7. The corona discharge assembly according to claim 6, characterized in that, the single conducting wire is a PCB copper clad conducting wire, wherein independent high voltage conducting wires are respectively welded at the tail end thereof in order to be connected with an external high voltage power supply.

8. The corona discharge assembly according to claim 7, characterized in that, the on-off of each high voltage conducting wire can be singly controlled.

9. The corona discharge assembly according to claim 1, wherein the ion reaction and storage ring is not in electrical contact with the metal corona cylinder, and the large opening end of the ion reaction and storage ring is in contact with a first grid of an ion gate to form an equipotential area between the interior of the large opening end and the first grid of the ion gate, in order to store ions.

10. An ion mobility spectrometer, characterized in that, the ion mobility spectrometer comprises:
    the corona discharge assembly according to claim 1;
    an ion gate composed of two opposite grids;
    a migration area, wherein the migration area comprises drift electrodes which are concentric equidistant circular ring electrodes; and
    a Faraday disc, wherein the rear of the Faraday disc is connected with a charge sensitive amplifier to read ion signals.

11. A method for corona discharge by using the corona discharge assembly according to claim 1, wherein at any moment, only one corona pin generates corona discharge, and the rest corona pins are suspended; the multiple corona pins are alternately loaded with a high voltage to work.

12. A computer program for controlling corona discharging of corona discharge assembly, characterized in that, controlling corona discharging of the corona discharge assembly according to claim 1, the computer program comprises the following step:
    wherein, only one corona pin generates corona discharge at any moment, the rest pins are suspended; and the multiple pins are alternately loaded with the high voltage to work.

13. A computer readable storage medium, characterized in that, the computer readable storage medium is used for storing the computer program according to claim 12.

* * * * *